(12) United States Patent
Aidam et al.

(10) Patent No.: US 12,216,042 B2
(45) Date of Patent: Feb. 4, 2025

(54) PHOTOACOUSTIC DETECTING DEVICE (71) Applicants: ECLYPIA, Grenoble (FR);
COMMISSARIAT A L'ENERGIE ATOMIQUE ET AUX ENERGIES ALTERNATIVES, Paris (FR)

(72) Inventors: Rolf Aidam, Wyhl (DE); Sébastien Barnola, Villard Bonnot (FR); Badhise Ben Bakir, Brézins (FR); Jean-Guillaume Coutard, Saint Pancrasse (FR); Kevin Jourde, Grenoble (FR)

(73) Assignees: ECLYPIA, Grenoble (FR); COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 18/641,107

(22) Filed: Apr. 19, 2024

(65) Prior Publication Data
US 2024/0353317 A1 Oct. 24, 2024

(30) Foreign Application Priority Data
Apr. 20, 2023 (EP) .................................. 23315088.7

(51) Int. Cl.
*G01N 21/17* (2006.01)
*A61B 5/145* (2006.01)
*G01N 29/24* (2006.01)

(52) U.S. Cl.
CPC .......... *G01N 21/1702* (2013.01); *A61B 5/145* (2013.01); *G01N 29/2418* (2013.01); *G01N 29/2425* (2013.01)

(58) Field of Classification Search
CPC .......... G01N 21/1702; G01N 29/2418; G01N 29/2425; A61B 5/145
See application file for complete search history.

(56) References Cited

U.S. PATENT DOCUMENTS 8,328,396 B2 12/2012 Capasso et al.
2016/0306079 A1* 10/2016 Arbabi ................. G02B 5/0268
(Continued)

OTHER PUBLICATIONS

European Search Report dated Sep. 22, 2023 for Application No. 23315088.7 (Year: 2023).*

(Continued)

*Primary Examiner* — Dominic J Bologna (57) ABSTRACT

A photoacoustic detecting device comprises a housing which houses: a lighting module, a photoacoustic cell, comprising an surface contact intended to be placed in contact with the medium to analyse, a photoacoustic cavity extending from the surface contact to a top of the photoacoustic cell, at least one window closing the top of the photoacoustic cell or the contact surface of the photoacoustic cell, at least one subwavelength pattern located on a surface of said window, said subwavelength pattern being configured to focus the light beam on an surface of interest of the medium to analyse, a sensor, linked to the cavity, the sensor being configured to detect a generated signal, said generated signal being generated in the photoacoustic cavity by a photothermic effect in the medium, and wherein the photoacoustic cell, the window and the subwavelength pattern are formed on a single silicon wafer.

11 Claims, 4 Drawing Sheets

(56) References Cited

U.S. PATENT DOCUMENTS

| | | | |
|---|---|---|---|
| 2020/0067281 A1 | 2/2020 | Curwen et al. | |
| 2022/0205901 A1* | 6/2022 | Coutard | G01N 21/1702 |
| 2022/0364981 A1* | 11/2022 | Lauwers | G01N 21/1717 |
| 2023/0266291 A1* | 8/2023 | Myrick | H10K 30/00 |

OTHER PUBLICATIONS

Yunfei Zhao et al. "Enhanced photoacoustic detection using photonic crystal substrate" Applied Physics Letters, Apr. 23, 2014, 104, 161110-1 to 161110-5, Ames, Iowa 50011, USA.

Sun-Goo Lee et al. "Reflection minimization at two-dimensional photonic crystal interfaces" Optics Express, vol. 16, No. 6, Mar. 13, 2008, pp. 4270-4277.

Sanja Hadzialic et al. "Two-Dimensional Photonic Crystals Fabricated in Monolithic Single-Crystal Silicon" IEEE Photonics Technology Letters, vol. 22, No. 2, Jan. 15, 2010, pp. 67-69.

"Topological photonic crystal made of silicon" Jan. 19, 2017, retrieved Nov. 15, 2022 from https://phys.org/news/2017-01-topological-photonic-crystal-silicon.html.

Raji Shankar et al. "Mid-infrared photonic crystal cavities in silicon" Optics Express, vol. 19, No. 6, Mar. 2011, pp. 5579-5586.

Maxime Guaisa et al. "Dielectric flat lens for the MIR region" Proceedings of SPIE, vol. 11261, 1126106-1 to 1126106-9, 2020, Palaiseau, France.

J. Fonollosa et al. "Design and fabrication of silicon-based mid infrared multi-lenses for gas sensing applications" Sensors and Actuators, Nov. 21, 2007, B 132 (2008) 498-507.

Amir Arbabi et al. "Efficient dielectric metasurface collimating lenses for mid-infrared quantum cascade lasers" Optics Express, vol. 23, No. 26, Dec. 17, 2015, DOI: 10.1364/OE.23.033310.

Nanfang Yu et al. "Quantum cascade lasers with integrated plasmonic antenna-array collimators" Optics Express, vol. 16, No. 24, Nov. 10, 2008, pp. 19447-19461.

Wim Bogaerts et al. "Fabrication of Ultra-Compact Photonic Structures in Silicon-on-Insulator (SOI) Using 248 nm Deep UV Lithography" ICTON, 2002.

A. Gilere et al. "Downsizing and Silicon Integration of Photoacoustic Gas Cells" International Journal of Thermophysics (2020) 41:16, Jan. 8, 2020, pp. 1-18.

JG Coutard et al. "Micro PA detector: pushing the limits of mid IR photoacoustic spectroscopy integrated on silicon" Proc. of SPIE vol. 11285, Feb. 26, 2020, p. 1128513.

European Search Report and Written Opinion dated Sep. 22, 2023 for Application No. 23315088.7.

* cited by examiner

PHOTOACOUSTIC DETECTING DEVICE

FIELD OF THE INVENTION

The present invention relates to a photoacoustic detecting device for measuring a parameter of interest in a medium.

BACKGROUND OF THE INVENTION

Photoacoustic detection can be used in the field of sensing devices, in particular to detect parameters of interest such as chemical components in a medium. The medium can be an organic tissue, such as the skin of a human being.

Photoacoustic detection is based on the irradiation of a medium M to be analyzed by a light beam emitted by a light source. The light beam is a light beam of a chosen wavelength. The wavelength is chosen according to the type of parameter of interest to be measured. Different types of light sources can be used, depending on the desired application.

The photoacoustic detection may be based on the detection of a pressure wave caused by a thermal wave. The thermal wave is generated by the absorption of the light beam by the medium. This absorption creates a local heating of the chemical components of the medium, where the light beam was absorbed. The thermal wave propagates in the medium M before propagating outside the medium. More precisely, when the thermal wave leaves the medium, after its diffusion, a pressure variation is generated, which can be detected. The passage of a thermal wave to an acoustic wave takes place in a photoacoustic cavity acting as a thermoacoustic transducer, and then a microphone-type sensor captures the acoustic wave by acting as an acoustoelectric transducer.

Photoacoustic detection can be made specific to particular chemical compounds by adjusting the wavelength of the light beam. Specifically, the wavelength can be adjusted to match an absorption peak of the component being analyzed. Indirect photoacoustic detection then provides a non-invasive way to analyze a medium of interest. Many photoacoustic detection devices have been developed. In particular, such devices have been developed to measure glucose levels in the epidermis of a person.

These photoacoustic sensing devices typically include a photoacoustic cell, a light source emitting a light beam, a guiding element guiding the light beam to the photoacoustic cell, and at least one transducer capable of detecting a signal generated in the photoacoustic cell by the photothermal effect in the medium in response to irradiation of the medium by the light beam.

A first requirement related to these detection devices is that they may be intended to be worn continuously, i.e. constantly, by a person. They must therefore be compact enough not to disturb the person wearing them. In other cases, the devices can be embedded in other devices and must therefore also be sufficiently compact to allow their integration.

Another requirement related to these detection devices is that, to provide an accurate measurement of the parameter of interest to analyse, the surface of the medium to be illuminated by the light source must be as small as possible. In other words, the divergence of the light beam reaching the medium must be as small as possible.

The present invention aims to propose a photoacoustic detecting device meeting at least partially the requirements presented above.

BRIEF SUMMARY OF THE INVENTION

Thus, the invention relates to photoacoustic detecting device for measuring a parameter of interest in a medium to analyse, the photoacoustic detecting device comprising:
  a housing comprising a cover and a baseplate, wherein the baseplate comprises an aperture, said housing being configured to house:
  at least one lighting module configured to emit at least one light beam,
  a photoacoustic cell, comprising an surface contact accessible from the aperture of the baseplate, said surface contact being intended to be placed in contact with the medium to analyse, the photoacoustic cell further comprising a photoacoustic cavity extending from the surface contact to a top of the photoacoustic cell, wherein said top and said surface contact are open,
  at least one window closing the top of the photoacoustic cell or the contact surface of the photoacoustic cell,
  at least one subwavelength pattern located on a surface of said window, said subwavelength pattern being configured to focus the light beam on an surface of interest of the medium to analyse,
  a sensor, linked to the cavity, the sensor being configured to detect a generated signal, said generated signal being generated in the photoacoustic cavity by a photothermic effect in the medium to analyse in response to the irradiation of said medium by the light beam,
  and wherein the photoacoustic cell, the window and the subwavelength pattern are formed on a single silicon wafer.

Thanks to these provisions, the detecting device presents several advantages upon the detecting device of the art. First, the use of a subwavelength pattern allows the focusing of the beam on an area of interest of the medium, leading to accurate measurement. Second, the subwavelength pattern is directly implemented on the surface of the window, such that it integrates perfectly within the device, without requiring a dedicated place in the device, therefore limiting the overall size of the device. Third, the implementation of the photoacoustic cell, window and subwavelength pattern on a single silicon wafer also allows to reduce the overall size of the device since no other components, taking space, are required. The combination of a focusing element and the photoacoustic cell into one single component is then particularly advantageous regarding the overall size of the device.

According to different aspects, it is possible to provide the one and/or the other of the characteristics below taken alone or in combination.

In an embodiment, a top surface of the window comprises a subwavelength pattern and a bottom surface of said window comprises another subwavelength pattern.

The device may then comprise two subwavelength patterns, one on each surface of the window. With this configuration, both subwavelength patterns may focus the light beam such that the focusing may be much more efficient.
the window may be closing the top of the photoacoustic cell of the contact surface of the photoacoustic cell.

In an embodiment, the window is a first window, said detecting device further comprising a second window, wherein the second window is configured to:
  close the top of the photoacoustic if the first window closes the contact surface of the photoacoustic cell, or,
  close the contact surface of the photoacoustic cell if the first window closes the top of the photoacoustic cell, wherein a surface of said second window comprises a subwavelength pattern.

In an embodiment, a top surface of the second window comprises a subwavelength pattern and a bottom surface of the second window comprises another subwavelength pattern.

According to the above-mentioned embodiment, the device may then comprise up to four subwavelength patterns, but can also comprise one, two or three subwavelength patterns. Numerous placement combinations of the subwavelength patterns may then be implemented depending on the need. All the subwavelength patterns may have the same functions or at least two of the subwavelength patterns may have different functions.

The window closing the top may be referred to as the top window and the window closing the contact surface may be referred to as the bottom window.

In an embodiment, the detecting device comprises a plurality of lighting modules, each being configured to emit a light beam, wherein the at least one subwavelength pattern is further configured to collimate the light beams emitted by each of the lighting modules.

Hence, furthermore to focus the beam, the at least one subwavelength pattern is configured to collimate the light beams of several lighting modules. It avoids the need to use a dedicated component, therefore even more reducing the overall size of the device.

If the device comprises more than one subwavelength pattern, the beam collimating function can be performed by one (or more) subwavelength pattern, while the focusing function can be performed by another (or several others) subwavelength pattern. In variation, all the subwavelength pattern arrays may perform the function of focusing and beam collimating.

In an embodiment, the at least one subwavelength pattern is further configured such that the light beam reaching the medium is a spot like beam.

For example, at least one subwavelength pattern is configured to transform a plane wave light beam to a spot like light beam. This is particularly efficient to obtain a small surface of interest to obtain more accurate measurements.

Hence a subwavelength pattern can be configured to perform several functions, comprising beam focusing, beam collimating and/or beam transforming.

If the device comprises more than one subwavelength pattern, the transforming function can be performed by one (or more) subwavelength pattern, while the focusing function can be performed by another (or several others) subwavelength pattern. In variation, all the subwavelength pattern may perform the function of focusing and transforming the light beam.

If the device comprises several lighting module(s) and more than one subwavelength pattern, the transforming function can be performed by one (or more) subwavelength pattern, the beam focusing function can be performed by one (or more) subwavelength pattern, and the collimating function can be performed by another (or several others) subwavelength pattern. In variation, all the subwavelength patterns may perform the function of focusing, collimating and optionally transforming the light beam if necessary.

In an embodiment, a surface of a window, said surface not comprising a subwavelength pattern, comprises antireflective properties.

In an embodiment, the at least one lighting module comprises a quantum cascade laser configured to emit a light beam in the mid infrared wavelength.

In an embodiment, the lighting module is configured to be placed perpendicularly to a plane defined by the window.

Hence, no further equipment needed.

In an embodiment, the lighting module is configured to be placed in parallel with a plane defined by the window.

Hence, only a mirror redirecting light would be needed. Advantageous if the overall thickness of the device needs to be reduced, with comparison to the perpendicular placement of the lighting module.

In an embodiment, said subwavelength pattern(s) further comprise anti reflective properties regarding a wavelength of the light beam.

The diffractiveness of the light beam is therefore limited or even eliminated. Such antireflective property may be obtained with the pattern of the subwavelength pattern.

In an embodiment, the pattern of the subwavelength pattern is either period or non-periodic.

A periodic subwavelength pattern may be used when the light beam is Gaussian or circular, and a non-periodic subwavelength pattern may be used when the light beam is not Gaussian nor circular.

BRIEF DESCRIPTION OF THE DRAWINGS

Embodiments of the invention will be described below with reference to the drawings, described briefly below.

In the drawings, identical references designate identical or similar objects.

DETAILED DESCRIPTION OF THE INVENTION

In a particular application, the photoacoustic detecting device 1 is particularly suitable for measuring a parameter of interest in a medium M to be analysed. The medium may be solid or liquid.

In a non-limiting example, the photoacoustic detecting device 1 (or "detecting device 1" in the following description) is intended to be worn by a person P. The medium M may be an organic tissue such as the skin of the person P wearing the detecting device 1.

A parameter of interest may be a chemical component present in the skin of the person P, such as molecules. The parameter of interest may comprise glucose, cholesterol, triglyceride, urea, albumin, and/or alcohol. This list is non exhaustive, and several other parameters of interest may be measured.

The measured parameters may then be analysed to determine a blood concentration of glucose, cholesterol and so on.

The sensing device 1 can be worn by a person at any location to measure a parameter of interest in the person's epidermis.

As an example, the detecting device 1 may be worn on the arm, or wrist, of a person P. In this configuration, the detecting device 1 may be fixed to the arm of the person P by means of a bracelet. Other fixing element may be used depending on the part of the body of the person.

The detecting device 1 may allow a continuous monitoring of the person P, by repeatedly measuring the parameters of interest of the person P, while it is worn.

Figure 1:
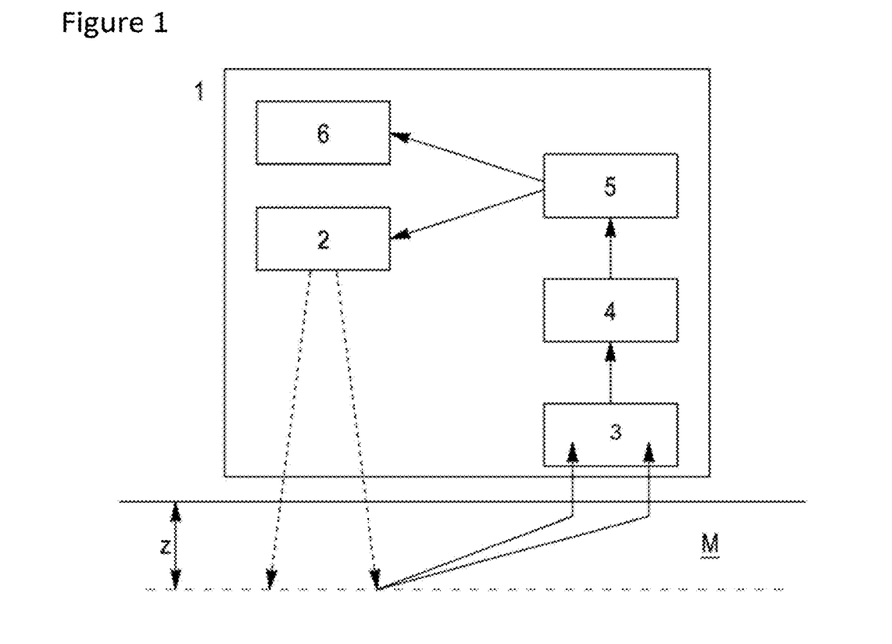
FIG. 1 represents a block schema of a photoacoustic detecting device.

FIG. 1 is a block diagram of the detecting device 1.

The detecting device 1 comprises:
at least one lighting module 2, configured to emit a light signal.
a sensor 3 acquiring a signal coming from the medium M,
a signal processing module 4 for analysing the signal detected by the sensor.

In an embodiment, the sensor 3 may be an acoustic sensor 3 detecting an acoustic signal generated in response to the irradiation of the medium M by the light signal The sensor 3 can be connected to the signal processing module 4 such that the signal processing module 4 receives a signal coming from the sensor 3.

In a non-limiting embodiment, the signal processing module 4 may comprise an analogic-to-numeric converter, converting the signal acquired by the sensor 3 to a numeric signal In another embodiment, the sensor 3 may directly transmit a numeric signal to the signal processing module 4.

The signal processing module 4 may be implemented in a processor (not shown) which may or not be remote from the detecting device 1.

The detecting device 1 may comprise other components. For example, the detecting device 1 may also comprise an adapting module 5 for adapting irradiation parameters of the lighting module 2 and a memory 6, for example. These components won't be further described.

In an embodiment, the lighting module 2 emits a light beam at a chosen wavelength, towards the medium M to be analysed. The chosen wavelength may be chosen according to the parameters of interest to be measured.

In this embodiment, the lighting module 2 may comprise a light source such as a laser, and more particularly a quantum cascade laser (QCL), or interband cascade laser (ICL), with external or internal cavities, or a light emitting diode (LED).

In another embodiment, the lighting module 2 may be able to emit a light beam with a tuneable wavelength. In this case, a tuneable external optical cavity or a tuneable internal optical cavity, such as Distributed Bragg Reflector (DBR) or a sampled DBR exploiting the Vernier effect, may be used.

In this embodiment, the lighting module 2 may comprise a light source such as a QCL with tuneable wavelengths.

In both above-described embodiments, the wavelength or wavenumber of the light beam emitted by the lighting module may be comprised between 1000 and 1250 cm 1. As an example, to detect glucose, the wavenumber may be 1034 cm 1, which corresponds to the absorption peak of the glucose.

In an embodiment, the detecting device 1 may comprise a plurality of lighting module 2, each comprising a light source as described above. In this embodiment, each lighting module 2 may emit a light beam at different wavelengths. In variant, some lighting module(s) 2 may emit a light beam at the same wavelength, while other lighting module(s) 2 may emit a light beam at a different wavelength. These two configurations may enable to perform a multispectral photoacoustic detection.

In still another configuration, each lighting module 2 may emit a light beam at the same wavelength.

As stated above, the light beam(s) are advantageously emitted in the mid-infrared, i.e. at wavelengths between 2 and 12 µm, preferably between 8 and 10 µm.

In the following paragraphs, the detecting device 1 is described as comprising only one lighting module 2, while it is understood that the same specification applies for a plurality of lighting modules 2.

The light beam emitted by the lighting module 2 propagates to the medium M and through it. This phenomenon is represented by the dotted arrows on FIG. 1. The light beam is absorbed by the constituents of the medium M under a depth z depending on the chosen wavelength of the light beam, the frequency of the light beam and on the composition of the medium M.

The absorption of the light beam energy causes a local heating of the medium M. As a consequence, a thermic signal propagates in the medium M (phenomenon illustrated by the full arrows on FIG. 2), in particular towards the surface of the medium M. Moreover, the thermic wave may create, outside the medium M, a pressure wave that propagates outside the medium M. Such a pressure wave may be detected by the acoustic sensor 3.

In an embodiment, the thermic wave may also be detected by means of a thermic sensor, such as a thermometer, not shown in the figures.

The detecting device 1 may comprise an acoustic and/or a thermic sensor 3. Other types of sensor 3 may be used.

Figure 2:
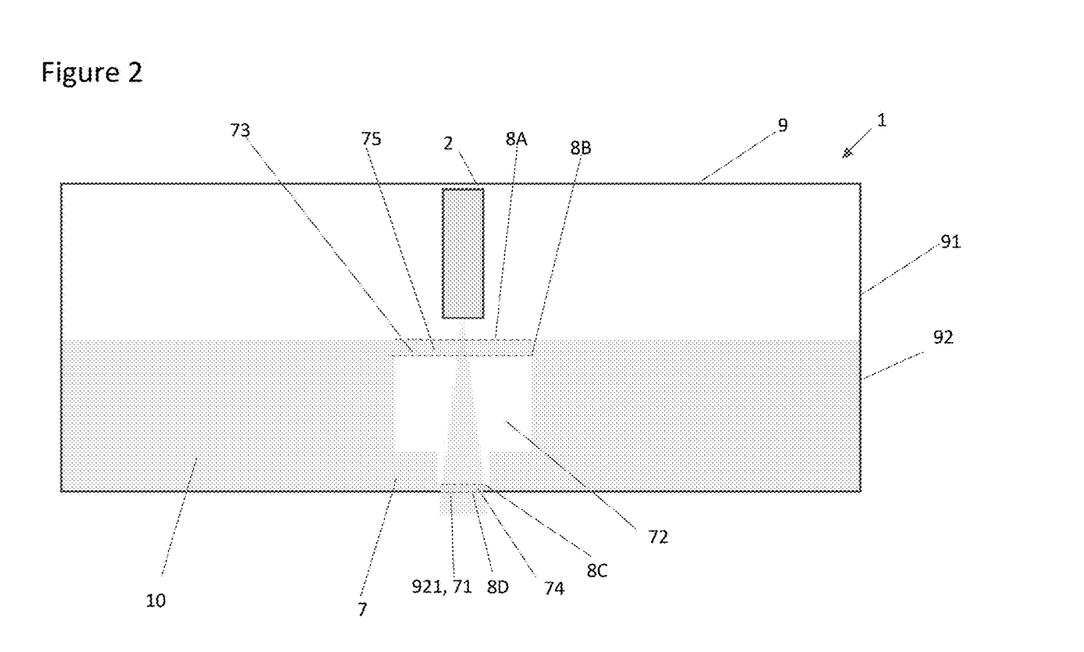
FIG. 2 represents a photoacoustic detecting device according to an embodiment.
Figure 3:
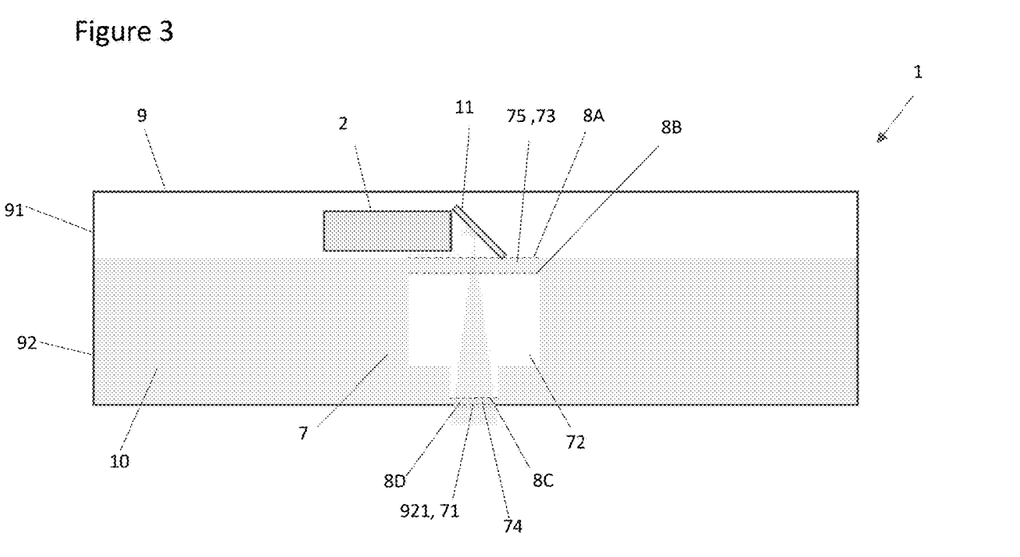
FIG. 3 represents a photoacoustic detecting device according to another embodiment.
Figure 4:
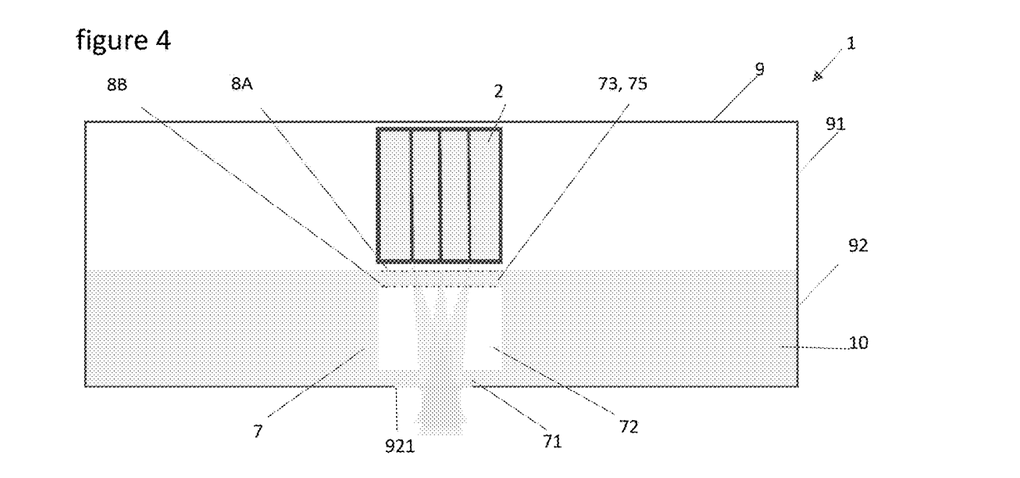
FIG. 4 represents a photoacoustic detecting device according to another embodiment.

FIGS. 2 to 4 illustrate several embodiments of the detecting device 1.

In the following description, the term horizontal is used to refer to the plane parallel to the plane formed by the baseplate 92. The term vertical is used to refer to a plane normal to the horizontal plane. The term bottom is used to refer to a region closer to the baseplate 92 and the term top is used to refer to a region closer to the cover 91.

Generally, the detecting device 1 comprises a housing 9 formed by a cover 91 and a baseplate 92. In use, the baseplate 92 is intended to be placed against the medium to analyse. More precisely, the baseplate 92 presents an aperture 921 intended to be placed against the medium to analyse.

Further to the lighting module(s) 2, the at least one sensor 3, the signal processing module 4, the adapting module 5 and the memory 6, the detecting device 1 comprises a photoacoustic cell 7 and at least one subwavelength pattern 8A, 8B, 8C, 8D.

The lighting module 2, the sensor 3, the photoacoustic cell 7, the subwavelength pattern 8A, 8B, 8C, 8D, the signal processing module 4, the adapting module 5 and the memory 6 are housed in the housing 9.

The lighting module 2 may be placed between the photoacoustic cell 7 and the cover 91.

The photoacoustic cell 7 comprises a contact surface 71 and a photoacoustic cavity 72.

The contact surface 71 may be located at the level of the aperture 921 of the baseplate 92. In one configuration, the contact surface 71 may emerge out of the aperture 921 of the baseplate 92 to be in contact with the medium to analyse. In another embodiment, the contact surface 71 may be flush with the baseplate 92 to be in contact with the medium to analyse.

The photoacoustic cavity 72 may extend from the contact surface 71 to a top 73 of the photoacoustic cell 7 near the lighting module(s).

The contact surface 71 of the photoacoustic cell may be closed by a window 74, hereafter called the bottom window 74. Advantageously, the bottom window is made in silicon.

The top 73 of the photoacoustic cell 7 may be closed by a window 75, hereafter called the top window 75. Advantageously, the top window is made in silicon.

In another embodiment, the contact surface 71 and the top 73 of the photoacoustic cell 7 may be closed, respectively, by a bottom window 74 and a top window 75. Advantageously, the top and bottom windows 75, 74 are made in silicon.

The light beam emitted by lighting module 2 is configured to be directed in the photoacoustic cavity 72, towards the photoacoustic cavity 72 until the light beam reaches the medium M to be analysed via the contact surface 71.

In case where the top 73 and/or the contact surface 71 are closed by a window, the light beam emitted by the lighting module(s) is configured to pass through said windows.

More precisely, the lighting module(s) 2 may be either placed in a vertical position, right above the top 73 of the photoacoustic cell 7, such that the light beam emitted by the lighting module(s) 2 is directly directed towards the photoacoustic cell 7 and more precisely directly towards the contact surface 71 of the photoacoustic cell 7 (see for example FIGS. 2 and 4).

This embodiment is advantageous since it allows to avoid the use of any additional optical element.

In another embodiment, the lighting module(s) is placed horizontally and a guiding element 11 such as a mirror is provided to redirect the light towards the photoacoustic cell 7 and more precisely directly towards the contact surface 91 of the photoacoustic cell 7 (see for example FIG. 3).

This embodiment may be advantageous since the integration of the lighting module(s) may be simplified. Moreover, it may diminish the thickness of the detecting device.

The detecting device 1 is further provided with at least one subwavelength pattern 8A, 8B, 8C, 8D, schematically represented by dotted lines on the figures.

The subwavelength pattern 8A, 8B, 8C, 8D is advantageously placed between the lighting module 2 and the medium to analyse M. More precisely, the subwavelength pattern 8A, 8B, 8C, 8D is provided between the lighting module(s) 2 and the aperture of the baseplate 92.

In an embodiment, a subwavelength pattern is provided at the top 73 of the photoacoustic cell 7. More precisely, a subwavelength pattern, hereafter called the first subwavelength pattern 8A, may be provided on a top surface of the top window 74.

In another embodiment, a subwavelength pattern, hereafter called the second subwavelength pattern 8B, may be provided on a bottom surface of the top window 74.

In another embodiment, two subwavelength patterns may be provided at the top 73 of the photoacoustic cell. More precisely, a first subwavelength pattern 8A, may be provided on a top surface of the top window 74 and a second subwavelength pattern 8B, may be provided on a bottom surface of the top window 74.

In another embodiment, a subwavelength pattern is provided at the contact surface 71 of the photoacoustic cell 7.

More precisely, a subwavelength pattern, hereafter called the third subwavelength pattern 8C, may be provided on a top surface of the bottom window 75.

In another embodiment, a subwavelength pattern, hereafter called the fourth subwavelength pattern 8D, may be provided on a bottom surface of the bottom window 75.

In another embodiment, two subwavelength patterns may be provided at the contact surface 71 of the photoacoustic cell. More precisely, the third subwavelength pattern 8C, may be provided on a top surface of the bottom window 75 and the fourth subwavelength pattern 8D, may be provided on a bottom surface of the bottom window 75.

The detecting device 1 may comprise one of the first, second, third, fourth subwavelength pattern 8A, 8B, 8C, 8D or a combination of two of the first, second, third, fourth subwavelength patterns 8A, 8B, 8C, 8D, or a combination of three of the first, second, third, fourth subwavelength patterns 8A, 8B, 8C, 8D or the four subwavelength patterns 8A, 8B, 8C, 8D. This last embodiment is illustrated on FIGS. 2 and 3 as a non-limitative example.

Advantageously, the photoacoustic cell 7 and the subwavelength pattern(s) 8A, 8B, 8C, 8D provided in the detecting device 1 are formed in a single silicon wafer 10.

The photoacoustic cavity 92 is directly formed inside the silicon wafer 10, i.e. by hollowing out the silicon wafer 10.

In the following description, the term "subwavelength pattern 8A, 8B, 8C, 8D" is used to refer indifferently to the first, second, third and/or fourth subwavelength patterns 8A, 8B, 8C, 8D. In other words, if the term "subwavelength pattern 8A, 8B, 8C, 8D" is used, it means that the feature described in reference with this term may apply to the first, second, third and/or fourth subwavelength patterns 8A, 8B, 8C, 8D.

Moreover, the use of the term "subwavelength pattern 8A, 8B, 8C, 8D" may refer to any configuration of the detecting device among which the detecting device 1 may comprise one of the first, second, third, fourth subwavelength pattern 8A, 8B, 8C, 8D or a combination of two of the first, second, third, fourth subwavelength patterns 8A, 8B, 8C, 8D, or a combination of three of the first, second, third, fourth subwavelength patterns 8A, 8B, 8C, 8D or the four subwavelength patterns 8A, 8B, 8C, 8D.

Generally, a first function of the subwavelength pattern 8A, 8B, 8C, 8D is to focus the light beam emitted by the lighting module(s) 2.

More precisely, without the subwavelength pattern 8A, 8B, 8C, 8D, the light beam emitted by the lighting module(s) may be divergent, leading to photoacoustic cell side walls absorption and therefore to a too large measurement area. Indeed, to obtain accurate measure of the parameter of interest in the medium M, the measurement area must be as small as possible. Typically, a surface of interest for performing accurate measurement should be between 0.2 to 5 mm, preferably between 0.8 to 1.2 mm.

The subwavelength pattern 8A, 8B, 8C, 8D may therefore be designed to focus the light beam on the surface of interest.

The pattern, i.e. the number, size (i.e. diameter for example) and particular position of the unit cells, is determined to perform such focusing.

Figure 5A:
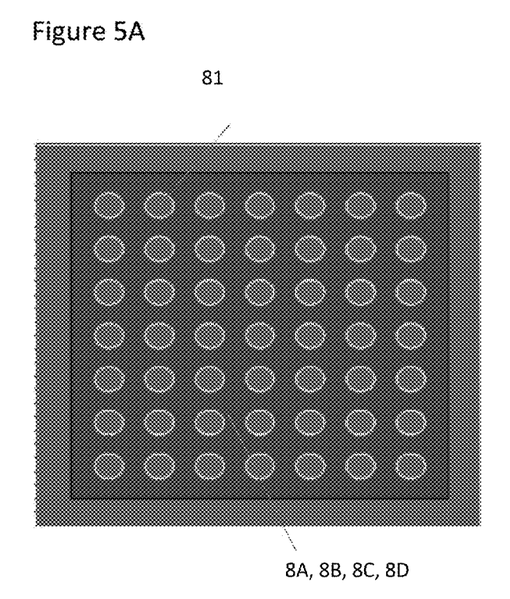
FIG. 5A represents an example of the subwavelength pattern.
Figure 5B:
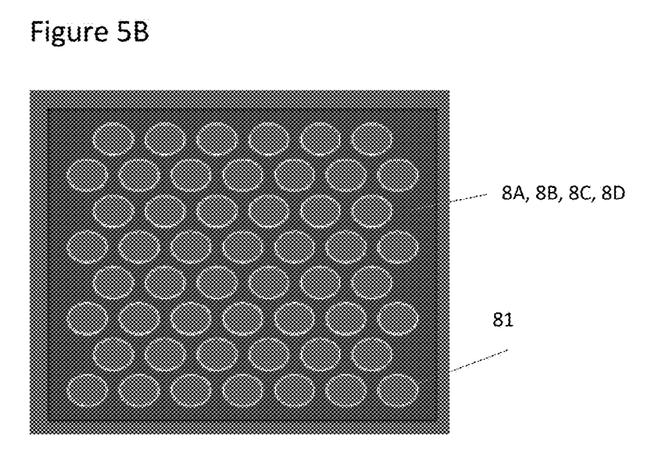
FIG. 5B represents another example of the subwavelength pattern.

In an embodiment, the subwavelength pattern(s) 8A, 8B, 8C, 8D may be periodic, i.e. the pattern of the subwavelength pattern(s) may have a periodic structure. FIGS. 5A and 5B illustrate an example of a periodic subwavelength pattern. Generally, the periodic subwavelength pattern 8A, 8B, 8C, 8D is formed of a 2D array of unit cells 81 disposed on a square (FIG. 5A) or hexagonal lattice (FIG. 5B). A unit cell 81 is formed of a pillar and/or a hole.

The unit cells 81 of the periodic subwavelength pattern 8A, 8B, 8C, 8D may be arranged according to a period in the range of 5 to 10 times shorter than the wavelength of the light beam emitted by the lighting module(s) 2. As a non-limitative example, for a light beam of a wavelength pertaining to the middle infrared, the period may be around 0.5 μm or less.

Such periodic subwavelength pattern may be used for light beam being Gaussian or circular.

Figure 6:
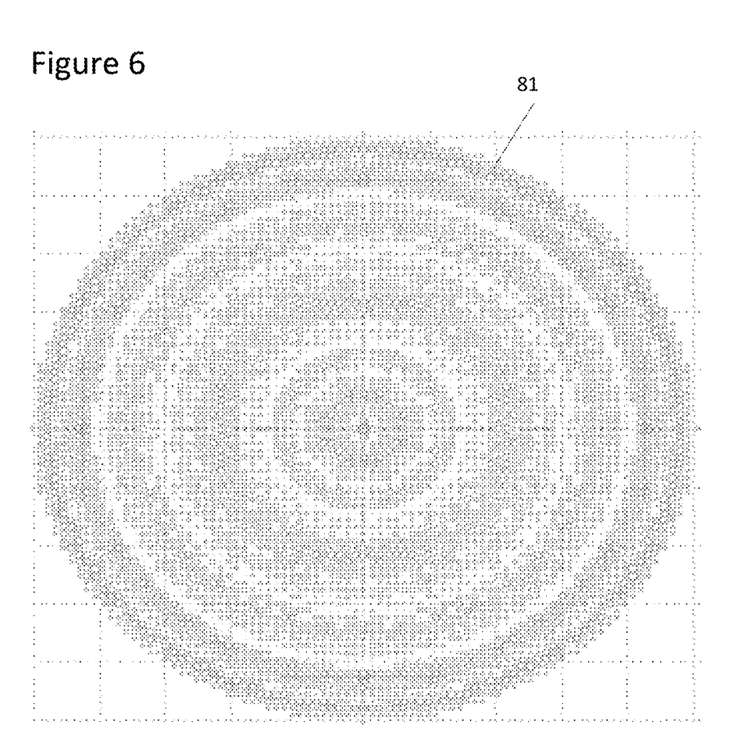
FIG. 6 represents another example of the subwavelength pattern.

In variant, the subwavelength pattern(s) 8A, 8B, 8C, 8D may not be periodic. FIG. 6 illustrates an example of a subwavelength pattern formed of a 2D array of unit cells 81, where the unit cells 81 are pillars and/or holes, arranged in a non-periodic structure. Each square represents a unit cell 81 on FIG. 6. A non-periodic subwavelength pattern may be used for light beam which is not Gaussian or circular.

If the detecting device comprises more than one subwavelength pattern, some subwavelength pattern(s) may have a periodic structure while some other(s) may have a non-periodic structure. In variant, all the subwavelength patterns may be periodic, or all the subwavelength patterns may be non-periodic.

In an embodiment, the structure of a non-periodic subwavelength pattern is obtained by a simulation procedure.

First, the simulation procedure stars with the analysis of the meta-atom properties of each unit cell 81, such as the phase-change induced by the unit cells 81, and the transmission of the incident light through the meat-atom, as a function of the width of the elementary pattern or equivalently of a unit cell 81. With this analysis, the phase change as a function of the variation of an opto-geometrical parameter is obtained. The opto-geometrical parameter is generally the width such that f (width)=phase change.

This analysis may be performed with the rigorous coupled wave analysis (RCWA).

Following this analysis, a range is chosen to cover at least a 360° phase change.

A phase profile is then defined. In the defined phase profile, each corresponding unit cell 81 is attributed locally.

The layout geometry is completed once all the desired phase profile is addressed by the unit cells (or meta-atoms).

In the case where the phase profile is not known, an inverse problem is to be solved first by performing a numerical optimization. For given inputs, for example a spatial energy distribution, and given outputs, for example a farfield pattern or a specific spatial distribution at a specific point, a mathematical solver may automatically generate the optimized phase profile.

Moreover, each interface silicon/air at the level of the bottom and top window 73, 74 requires to be anti-reflective.

In other words, when a subwavelength pattern 8A, 8B, 8C, 8D is provided at the bottom and/or top window 73, 74, the subwavelength pattern 8A, 8B, 8C, 8D presents anti-reflective properties.

Also, if a subwavelength pattern 8A, 8B, 8C, 8D is not provided on a top or bottom surface of the top and/or bottom window, the top or bottom surface with no subwavelength pattern 8A, 8B, 8C, 8D also presents antireflective properties. Such anti-reflective properties may be provided with an antireflecting coating. Such coating may be a full-surface anti-reflective (AR) ZnS coating with a thickness of 1067 nm.

The antireflective properties of the subwavelength pattern 8A, 8B, 8C, 8D may be obtained with the pattern of said subwavelength pattern 8A, 8B, 8C, 8D.

For example, the average form factor of the subwavelength pattern 8A, 8B, 8C, 8D may be around 50% and the edge depth of the unit cells 81 may be comprised between 0.2 and 5 µm, preferably around 0.5 µm.

In case where several lighting modules 2 are used, the subwavelength pattern 8A, 8B, 8C, 8D may also have the function of collimating the light beams into one. Such collimating function may also be obtained by the pattern of the subwavelength pattern 8A, 8B, 8C, 8D.

Furthermore, the particular pattern of the subwavelength pattern 8A, 8B, 8C, 8D allows the subwavelength pattern 8A, 8B, 8C, 8D to transform the light beam(s) so as to obtain a spot like beam when the light beam reaches the area of interest.

The light beam may take several forms (i.e. plane wave, Gaussian beam or spot-like beam raising from a facet of a laser device) by passing through the subwavelength pattern, as long as it comes in the spot like beam form when reaching the area of interest.

In some embodiments, the above-mentioned functions, i.e. the beam focusing, the beam collimation and optionally the beam transformation to spot like beam if necessary, may be implemented on separated subwavelength patterns array 8A, 8B, 80, 8D.

More precisely, when the detecting device comprises one subwavelength pattern among the first, second, third and fourth subwavelength pattern 8A, 8B, 8C, 8D, said subwavelength pattern may be configured to perform the focusing of the light beam, the beam collimation of a plurality of light beams when several lighting modules 2 are used, and/or optionally the beam transformation to a spot like beam if necessary.

If the detecting device comprises two subwavelength patterns among the first, second, third and fourth subwavelength pattern 8A, 8B, 8C, 8D, one of the two subwavelength patterns may be configured to perform one or two of the functions of focusing of the light beam, the collimating the beams when several lighting modules 2 are used, and optionally transforming the beam to a spot like beam if necessary, while the other subwavelength pattern performs the function(s) not performed by the other subwavelength pattern. And so on.

Hence, one subwavelength pattern may at least perform one function but can perform several functions. Several subwavelength pattern may perform the same functions for more efficiency. For example, two subwavelength patterns may perform the focusing function, among others.

Regarding the photoacoustic detection, a thermic wave is generated under the effect of the absorption by the medium of the light beam emitted by the lighting module. Such absorption creates a local heating of chemical components in the medium, where the light beam has been absorbed. The thermic wave propagates in the medium M before propagating outside the medium. When the thermic wave comes out of the medium, after its propagation, a pressure wave is generated, which propagates in the cavity 91 of the cell 7 where it can be detected. The pressure wave, i.e. an acoustic wave, is then induced by the photothermic effect.

The sensor 3 is located in the interior of the housing 9 and is preferably assembled to the photoacoustic cell 7, such that the sensor 3 can detect and measure the generated pressure wave. More precisely, the sensor may be assembled to the photoacoustic via a channel provided in the silicon wafer 10.

Regarding the fabrication process, standard silicon technology processes may be used, such as E-beam lithography or UV lithography. It is quite advantageous since the fabrication of the photoacoustic cell, window(s) and subwavelength pattern(s) may then be implemented in standard process, therefore limiting the cost.

As an example, once the pattern of the subwavelength pattern has been designed as explained above, the pattern is transferred to a photolithographic mask. Then, the standard silicon UV or beam lithography is implemented to get the single silicon wafer comprising the photoacoustic cell, the window(s) and the subwavelength pattern(s).

For example, on the same wafer the photoacoustic cell will be first made and during a second step, the subwavelength pattern(s) will be made.

While exemplary embodiment of the invention has been described with reference to two main embodiments, it will be understood by those skilled in the art that various changes, omissions and/or additions may be made, and equivalents may be substituted for elements thereof without departing from the spirit and scope of the invention. In addition, many modifications may be made to adapt a particular situation or material to the teachings of the invention without departing from the scope thereof. Therefore, it is intended that the invention is not limited to the particular embodiment disclosed as the best mode contemplated for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

The invention claimed is:

1. A photoacoustic detecting device for measuring a parameter of interest in a medium to analyse, the photoacoustic detecting device comprising:
    a housing comprising a cover and a baseplate, wherein the baseplate comprises an aperture, said housing being configured to house:
    at least one lighting module configured to emit at least one light beam,
    a photoacoustic cell, comprising a contact surface accessible from the aperture of the baseplate, said contact surface being intended to be placed in contact with the medium to analyse, the photoacoustic cell further comprising a photoacoustic cavity extending from the contact surface to a top of the photoacoustic cell, wherein said top and said surface contact are open,
    at least one window closing the top of the photoacoustic cell or the contact surface of the photoacoustic cell,
    at least one subwavelength pattern located on a surface of said window, said subwavelength pattern being configured to focus the light beam on a surface of interest of the medium to analyse,
    a sensor, linked to the photoacoustic cavity, the sensor being configured to detect a generated signal, said generated signal being generated in the photoacoustic cavity by a photothermic effect in the medium to analyse in response to the irradiation of said medium by the light beam, and wherein the photoacoustic cell, the window and the subwavelength pattern are formed on a single silicon wafer.

2. The photoacoustic detecting device according to claim 1, wherein a top surface of the window comprises a subwavelength pattern and a bottom surface of said window comprises another subwavelength pattern.

3. The photoacoustic detecting device according to claim 1, wherein the window is a first window, said photoacoustic detecting device further comprising a second window, wherein the second window is configured to:
    close the top of the photoacoustic cell if the first window closes the contact surface of the photoacoustic cell, or,
    close the contact surface of the photoacoustic cell if the first window closes the top of the photoacoustic cell, wherein
    a surface of said second window comprises a subwavelength pattern.

4. The photoacoustic detecting device according to claim 3, wherein a top surface of the second window comprises a subwavelength pattern and a bottom surface of the second window comprises another subwavelength pattern.

5. The photoacoustic detecting device according to claim 1, comprising a plurality of lighting modules, each being configured to emit a light beam, wherein the at least one subwavelength pattern is further configured to collimate the light beams emitted by each of the lighting modules.

6. The photoacoustic detecting device according to claim 1, wherein a surface of a window, said surface not comprising a subwavelength pattern, comprises antireflective properties.

7. The photoacoustic detecting device according to claim 1, wherein the at least one lighting module comprises a quantum cascade laser configured to emit a light beam in the mid infrared wavelength.

8. The photoacoustic detecting device according to claim 1, wherein the at least one lighting module is configured to be placed perpendicularly to a plane defined by the window.

9. The photoacoustic detecting device according to claim 1, wherein the at least one lighting module is configured to be placed in parallel with a plane defined by the window.

10. The photoacoustic detecting device according to claim 1, wherein said subwavelength pattern(s) further comprise anti reflective properties regarding a wavelength of the light beam.

11. The photoacoustic detecting device according to claim 1, wherein a pattern of the subwavelength pattern is either period or non-periodic.

* * * * *